US011607656B2

United States Patent
Iwama et al.

(10) Patent No.: US 11,607,656 B2
(45) Date of Patent: Mar. 21, 2023

(54) FIXED-BED MULTI-TUBULAR REACTOR FOR PRODUCING ALKENYL ACETATE

(71) Applicant: SHOWA DENKO K.K., Tokyo (JP)

(72) Inventors: Yasuhiro Iwama, Oita (JP); Maiko Ikushima, Oita (JP); Kazuki Umehara, Oita (JP); Mitsuru Tanaka, Oita (JP); Toshiyuki Maki, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 205 days.

(21) Appl. No.: 17/289,352

(22) PCT Filed: Oct. 28, 2020

(86) PCT No.: PCT/JP2020/040516
§ 371 (c)(1),
(2) Date: Apr. 28, 2021

(87) PCT Pub. No.: WO2021/124696
PCT Pub. Date: Jun. 24, 2021

(65) Prior Publication Data
US 2022/0314181 A1 Oct. 6, 2022

(30) Foreign Application Priority Data
Dec. 16, 2019 (JP) .............................. JP2019-226539

(51) Int. Cl.
*B01J 8/00* (2006.01)
*B01J 8/06* (2006.01)
(Continued)

(52) U.S. Cl.
CPC ............... *B01J 8/065* (2013.01); *B01J 8/001* (2013.01); *C07C 67/05* (2013.01); *B01J 2208/00061* (2013.01)

(58) Field of Classification Search
CPC ...... B01J 8/00; B01J 8/001; B01J 8/008; B01J 8/06; B01J 8/065; B01J 8/067;
(Continued)

(56) References Cited

U.S. PATENT DOCUMENTS

| 5,011,980 A | 4/1991 | Sano et al. |
| 7,074,364 B2 * | 7/2006 | Jahn ..................... B01J 19/0046 422/62 |

(Continued)

FOREIGN PATENT DOCUMENTS

| JP | 2-91045 A | 3/1990 |
| JP | 2002-212127 A | 7/2002 |

(Continued)

OTHER PUBLICATIONS

Anonymous: "Reactor Multipoint Thermocouples—Thermocouple Detector-Pyro Electric", May 2, 2012, pp. 1-7, XP055935900, Retrieved from the Internet: URL:http://pyro-electric.in/reactor-multipoint-temperature-thermocouples/[retrieved on Jun. 27, 2022].

(Continued)

*Primary Examiner* — Natasha E Young
(74) *Attorney, Agent, or Firm* — Sughrue Mion, PLLC

(57) ABSTRACT

A fixed-bed multi-tubular reactor for producing an alkenyl acetate by a gas phase catalytic oxidation reaction of a lower olefin, acetic acid and oxygen including a plurality of reaction tubes, a thermometer protection tube inserted into at least one of the plurality of reaction tubes, a thermometer inserted into the thermometer protection tube, and a shield disposed above the reaction tube into which the thermometer protection tube is inserted and attached to the thermometer protection tube, wherein an effective projection region of the shield entirely covers the inlet opening of the reaction tube into which the thermometer protection tube is inserted.

7 Claims, 17 Drawing Sheets

(51) Int. Cl.
*B01J 19/00* (2006.01)
*C07C 67/055* (2006.01)
*C07C 67/05* (2006.01)

(58) Field of Classification Search
CPC .... B01J 19/00; B01J 19/0006; B01J 19/0013; B01J 19/0053; B01J 2208/00; B01J 2208/00008; B01J 2208/00017; B01J 2208/00026; B01J 2208/00035; B01J 2208/00044; B01J 2208/00061; B01J 2208/00106; B01J 2208/00168; B01J 2208/00212; B01J 2208/06; B01J 2208/065; C07C 67/00; C07C 67/04; C07C 67/05; C07C 67/055
See application file for complete search history.

(56) References Cited

U.S. PATENT DOCUMENTS

| | | | |
|---|---|---|---|
| 7,534,339 B2* | 5/2009 | Matsumoto | B01J 8/001 422/312 |
| 8,063,778 B2* | 11/2011 | Johns | B01J 8/008 340/568.1 |
| 2003/0006026 A1 | 1/2003 | Matsumoto et al. | |
| 2008/0071109 A1 | 3/2008 | Yada et al. | |
| 2009/0163748 A1 | 6/2009 | Bank et al. | |
| 2015/0328611 A1 | 11/2015 | Yamauchi et al. | |

FOREIGN PATENT DOCUMENTS

| | | |
|---|---|---|
| JP | 2003-001094 A | 1/2003 |
| JP | 2004-526553 A | 9/2004 |
| JP | 2009-148757 A | 7/2009 |
| KR | 2001-0071587 A | 7/2001 |
| WO | 02/04392 A1 | 1/2002 |
| WO | 2005/110960 A1 | 11/2005 |

OTHER PUBLICATIONS

Series "Catalysts and Economy", "Transition of Vinyl Acetate Manufacturing Process and Its Prospect", 1993, pp. 467-470, vol. 35, No. 7.

International Search Report of PCT/JP2020/040516 dated Dec. 28, 2020 [PCT/ISA/210].

* cited by examiner

FIXED-BED MULTI-TUBULAR REACTOR FOR PRODUCING ALKENYL ACETATE

CROSS REFERENCE TO RELATED APPLICATIONS

This application is a National Stage of International Application No. PCT/JP2020/040516, now WO 2012/124696, filed Oct. 28, 2020, claiming priority to Japanese Patent Application No. 2019-226539, filed Dec. 16, 2019.

FIELD

The present invention relates to a fixed-bed multi-tubular reactor used in producing an alkenyl acetate, such as allyl acetate and vinyl acetate, from a lower olefin, acetic acid and oxygen by a gas phase catalytic oxidation reaction.

BACKGROUND

Allyl acetate is one of the important industrial raw materials used for manufacturing raw materials, such as solvents and allyl alcohol.

As a method for producing allyl acetate, there is a method in which propylene, acetic acid and oxygen are used as raw materials, and a gas phase reaction or a liquid phase reaction is used. As a catalyst used in this reaction, a catalyst in which palladium is used as a main catalyst component and an alkali metal or alkaline earth metal compound is used as a cocatalyst, and these are supported on a carrier is known and widely used. For example, JP H2-91045 A (Patent Literature 1) describes a method for producing allyl acetate using a catalyst in which palladium, potassium acetate, and copper are supported on a carrier.

On the other hand, vinyl acetate is an important industrial material used in a variety of fields, such as a paint, an adhesive, and a fiber treatment agent, as a raw material of a vinyl acetate resin, a raw material of polyvinyl alcohol, or a monomer for copolymerization with ethylene, styrene, an acrylate, or a methacrylate.

As a method for producing vinyl acetate, there is a method in which ethylene, acetic acid and oxygen are used as raw materials, and a gas phase reaction or a liquid phase reaction is used. As a catalyst used in this reaction, a catalyst in which palladium is used as a main catalyst component and an alkali metal or alkaline earth metal compound is supported on a carrier as a cocatalyst is known and widely used. For example, JP 2004-526553 A (Patent Literature 2) describes a method for producing vinyl acetate using a catalyst in which palladium, gold, and potassium acetate are supported on a carrier.

In the production process of an alkenyl acetate using the aforementioned catalyst, Patent Literature 1 and Series "Catalysts and Economy", Vol. 35, No. 7 (1993), pp. 467-470 (Non-Patent Literature 1) describe that it is necessary to continuously supply potassium acetate to the catalyst, since small amounts of potassium acetate leak out of the catalysts filled in the reaction tube during a process operation of a continuous reaction for a long period of time over several thousand hours in a unit.

As a reactor applied to the production of alkenyl acetate, a fixed-bed tubular reactor is generally used. A fixed-bed tubular reactor is one in which a catalyst (supported on a carrier) as a fixed-bed is filled in a reaction tube. A fixed-bed multi-tubular reactor is one having a plurality of reaction tubes among fixed-bed tubular reactors. A reaction substrate is supplied to the reaction tube in a gas phase state, and reacts in the catalyst layer, and a reaction product is discharged from the reaction tube. As the reaction tube, a straight reaction tube is often used from the viewpoint of equipment manufacturing, equipment maintenance, workability at the time of filling and replacing the catalyst, removal of reaction heat, etc. In many cases, the reaction tube is installed in a vertical direction from the viewpoint of workability of filling and extracting the catalyst.

In general, in order to observe the reaction state in the catalyst layer during the operation of an industrial manufacturing process, the catalyst layer temperatures of these reactors are monitored. A method for measuring a catalyst layer temperature includes, for example, as described in JP 2002-212127 A (Patent Literature 3), a method for measuring temperatures of reaction tubes in the longitudinal direction in which protection tubes (sheaths) are placed in several reaction tubes representing the entirety of the fixed-bed multi-tubular reactor before filling the catalyst, and thermocouples are inserted in these protection tubes.

Since the gas phase catalytic oxidation reaction is an exothermic reaction, a heat medium for heat removal is generally supplied to the outsides of the reaction tubes. By monitoring the temperature difference between the heat medium temperature outside the reaction tubes (shell temperature) and the catalyst layer temperatures, it is possible to observe how much reaction substrate is reacting at which position in the longitudinal direction of the catalyst layer. When uneven temperature distribution occurs, the plant can be operated so that the gas phase catalytic oxidation reaction proceeds stably and efficiently by controlling the reaction based on the uneven temperature distribution.

CITATION LIST

Patent Literature

[PTL 1] JP H2-91045 A
[PTL 2] JP 2004-526553 A
[PTL 3] JP 2002-212127 A

Non-Patent Literature

[NPL 1] Series "Catalysts and Economy", "Transition of Vinyl Acetate Manufacturing Process and Its Prospect", Vol. 35, No. 7 (1993), pp. 467-470

SUMMARY

Technical Problem

A thermocouple inserted into the reaction tube of the fixed-bed tubular reactor as described above can accurately measure the catalyst layer temperature, when only a gas is provided as a process fluid. However, the present inventors have found that, when this temperature measurement method is applied to a fixed-bed multi-tubular reactor for producing an alkenyl acetate and a long-term continuous reaction over several months is carried out, even though the reaction proceeds in the entirety of the fixed-bed multi-tubular reactor to produce a target reaction product (which means that the catalyst layer temperature is higher than the heat medium temperature (shell temperature) of the shell side (region where the heat medium flows outside the reaction tube) during the continuous reaction, due to the generation of the reaction heat), in practice, no temperature difference is observed between the catalyst layer temperature and the shell temperature, so that the catalyst layer temperature representing the entirety of the fixed-bed multi-tubular reactor cannot be monitored.

In view of the above circumstances, it is an object of the present invention to provide a reaction apparatus capable of correctly measuring a catalyst layer temperature inside a reaction tube, even when a process operation for a long period of time is carried out to produce an alkenyl acetate by a gas phase catalytic oxidation reaction of a lower olefin, acetic acid and oxygen using a fixed-bed multi-tubular reactor.

Solution to Problem

The present inventors have found that the above phenomenon is caused by the fact that a mist of an aqueous solution of an alkali metal acetate supplied to a fixed-bed multi-tubular reactor for producing vinyl acetate and allyl acetate attaches to a thermometer protection tube which is inserted into a reactor, and then forms a liquid droplet, which flows down over the thermometer protection tube, and is selectively supplied to a reaction tube into which the thermometer protection tube is inserted, whereby the amount of an alkali metal acetate supported by a catalyst in the reaction tube into which the thermometer protection tube is inserted excessively increases, and as a result, a catalytic activity decreases. In the reaction tube in which a catalyst having reduced catalytic activity is filled as described above, i.e., in the reaction tube into which a thermocouple is inserted, the amount of generated reaction heat is small, so that the temperature difference between the catalyst layer temperature in the reaction tube and the shell temperature is small. On the other hand, since the reaction proceeds properly in reaction tubes into which no thermocouple is inserted, the catalyst layer temperatures in these reaction tubes are correspondingly higher than the shell temperature, but are not reflected in a measured value of the catalyst layer temperature of the plant. Therefore, it may not be possible to appropriately operate the plant.

In view of the above, the present inventors have discovered that by providing a specific shield for preventing a liquid droplet of alkali metal acetate attached to a thermometer protection tube from being supplied to a reaction tube, into which the thermometer protection tube is inserted, over the thermometer protection tube, it is possible to prevent a liquid droplet of alkali metal acetate from being selectively supplied to the reaction tube into which the thermometer protection tube is inserted, thereby completing the present invention.

That is, the present invention encompasses [1] to [7] below.

[1]

A fixed-bed multi-tubular reactor for producing an alkenyl acetate, comprising:

a plurality of reaction tubes to which a raw material gas and a mist of an aqueous solution of an alkali metal acetate are supplied from an upper part of the fixed-bed multi-tubular reactor and which each have an inlet opening and an upper plane, a thermometer protection tube inserted into at least one of the plurality of reaction tubes from the upper part of the fixed-bed multi-tubular reactor, a thermometer inserted into the thermometer protection tube, and a shield disposed above the reaction tube into which the thermometer protection tube is inserted and attached to the thermometer protection tube, wherein an effective projection region of the shield entirely covers the inlet opening of the reaction tube into which the thermometer protection tube is inserted, wherein the effective projection region of the shield is an area on a reference plane obtained by projecting, in a perpendicular direction to the reference plane including the upper plane of the reaction tube into which the thermometer protection tube is inserted and extending in parallel with the upper plane, an area surrounded by line segments connecting points of the shield at which liquid droplets are separated from the shield and drop, when the mist of an aqueous solution of an alkali metal acetate contacts the shield and flows down as the liquid droplets.

[2]

The fixed-bed multi-tubular reactor according to [1], wherein the shield is a disk.

[3]

The fixed-bed multi-tubular reactor according to [2], wherein the diameter of the disk is larger than the inner diameter of the reaction tube.

[4]

The fixed-bed multi-tubular reactor according to any one of [1] to [3], wherein the alkali metal acetate is at least one selected from the group consisting of potassium acetate and cesium acetate.

[5]

The fixed-bed multi-tubular reactor according to any one of [1] to [4], wherein the number of the reaction tubes into which the thermometer protection tube is inserted is 3 to 10.

[6]

The fixed-bed multi-tubular reactor according to any of [1] to [5], wherein the thermometer is a thermocouple or a resistance thermometer.

[7]

A fixed-bed multi-tubular reactor for producing an alkenyl acetate, comprising:

a plurality of reaction tubes to which a raw material gas and a mist of an aqueous solution of an alkali metal acetate are supplied from an upper part of the fixed-bed multi-tubular reactor and which each have an inlet opening and an upper plane, a thermometer protection tube inserted into at least one of the plurality of reaction tubes from the upper part of the fixed-bed multi-tubular reactor, a thermometer inserted into the thermometer protection tube, and a shield disposed above the reaction tube into which the thermometer protection tube is inserted and attached to the thermometer protection tube, wherein an effective projection region of the shield does not overlap at all the inlet opening of the reaction tube into which the thermometer protection tube is inserted, wherein the effective projection region of the shield is an area on a reference plane obtained by projecting, in a perpendicular direction to the reference plane including the upper plane of the reaction tube into which the thermometer protection tube is inserted and extending in parallel with the upper plane, an area surrounded by line segments connecting points of the shield at which liquid droplets are separated from the shield and drop, when the mist of an aqueous solution of an alkali metal acetate contacts the shield and flows down as the liquid droplets.

Advantageous Effects of Invention

According to the present invention, since the catalyst layer temperature inside a reaction tube in the production of an alkenyl acetate can be measured accurately at all times, a measured value of the catalyst layer temperature can be used as an indicator for detecting a hot spot, an indicator for adjusting a supply amount of an alkali metal acetate, etc. Thus, the production efficiency of an alkenyl acetate can be maintained high over a long period of time.

DESCRIPTION OF EMBODIMENTS

Hereinafter, preferred embodiments of the present invention will be described, but the present invention is not limited to these embodiments only.

<Fixed-Bed Multi-Tubular Reactor>

A fixed-bed multi-tubular reactor for producing an alkenyl acetate according to one embodiment comprises a plurality of reaction tubes to which a raw material gas and a mist of an aqueous solution of an alkali metal acetate are supplied from an upper part of the fixed-bed multi-tubular reactor and which each have an inlet opening and an upper plane, a thermometer protection tube inserted into at least one of the plurality of reaction tubes from the upper part of the fixed-bed multi-tubular reactor, a thermometer inserted into the thermometer protection tube, and a shield disposed above the reaction tube into which the thermometer protection tube is inserted and attached to the thermometer protection tube.

Figure 1:
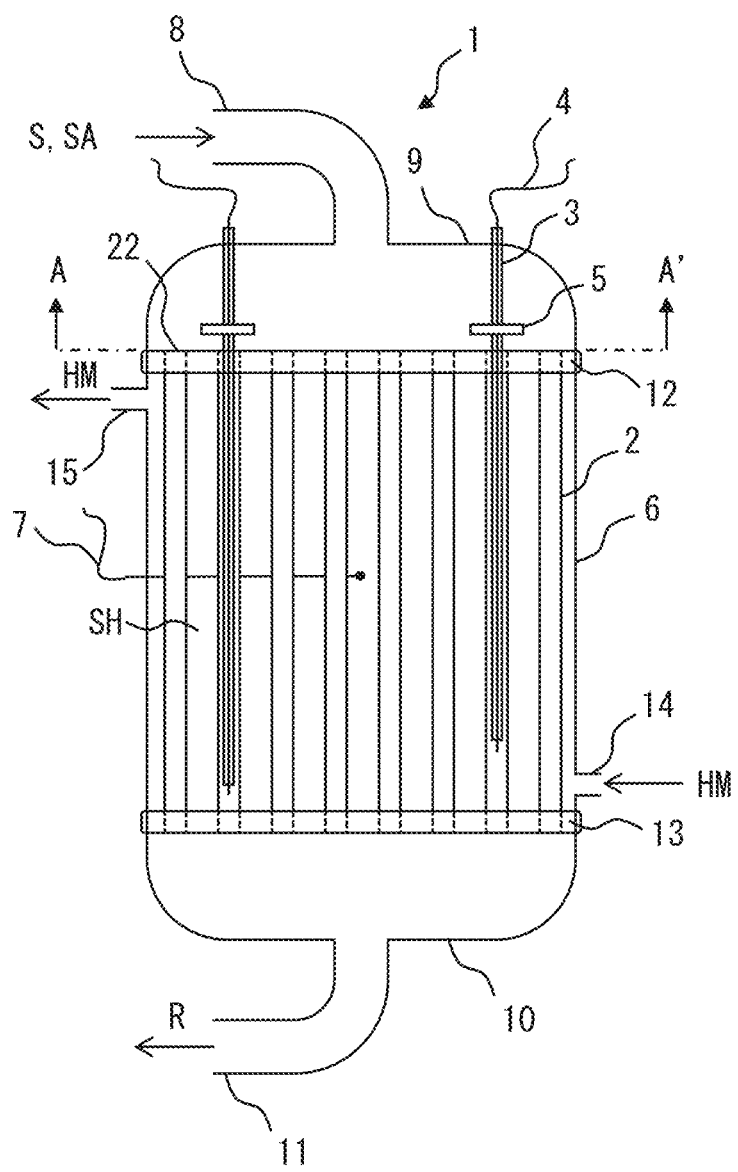
FIG. 1 It is a schematic longitudinal sectional view of a fixed-bed multi-tubular reactor according to an embodiment.
Figure 1A:
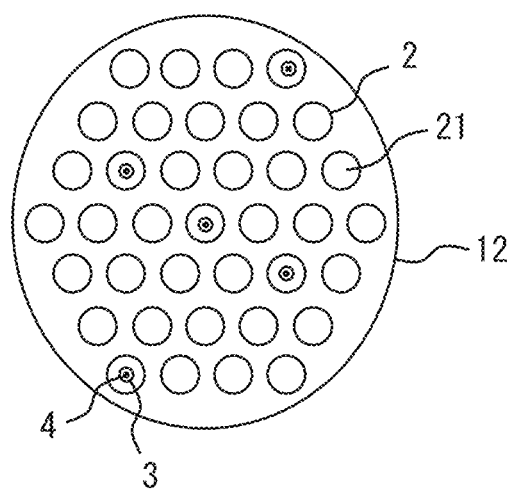
FIG. 1A It is a top view of a plane A-A' of the fixed-bed multi-tubular reactor of FIG. 1.

FIG. 1 is a schematic longitudinal sectional view of a fixed-bed multi-tubular reactor (hereinafter referred to simply as a "reactor") according to one embodiment, and FIG. 1A is a top view of a plane A-A' of the reactor 1 of FIG. 1. As shown in FIG. 1 and FIG. 1A, the reactor 1 includes a plurality of reaction tubes 2 each having an inlet opening 21 and an upper plane 22, a thermometer protection tube 3 inserted into at least one of the plurality of reaction tubes 2, a thermometer 4 inserted into the thermometer protection tube 3, and a shield 5 attached to the thermometer protection tube 3.

The inside of the reaction tube 2 is filled with a catalyst (supported on a carrier, not shown) as a fixed-bed. A reaction substrate is supplied as a raw material gas S in a gas phase from a raw material gas supply 9 located at an upper part of the reactor 1 through a supply line 8 to the reaction tube 2, and reacts in a catalyst layer to generate a reaction product R. After being discharged from the reaction tube 2, the reaction product R is collected in a reaction product discharge section 10 located at a lower part of the reactor 1 and discharged through an extraction line 11. The reaction tube 2 is preferably a straight tube from the viewpoint of equipment manufacturing, equipment maintenance, workability at the time of filling and replacing the catalyst, removal of reaction heat, etc. The reaction tube 2 is preferably installed in a vertical direction from the viewpoint of workability of filling and extracting the catalyst. The upper end and the lower end of the reaction tube 2 are fixed by an upper fixing plate 12 and a lower fixing plate 13, respectively.

Since the gas phase catalytic oxidation reaction for synthesizing an alkenyl acetate is an exothermic reaction, a system for removing reaction heat from the outside of the reaction tube 2 is required. Even though there are no particular limitations on the inner diameter, outer diameter, length, material, and reaction heat removal equipment of the reaction tube 2, and a reaction heat removal method, the inner diameter of the reaction tube 2 is preferably 10 to 40 mm, and the length thereof is preferably 1 to 8 m, from the viewpoint of removal efficiency of reaction heat, the balance between a heat exchange area and a pressure loss inside the reaction tube, etc. Due to the limitations in increasing the inner diameter of the reaction tube 2 in terms of removal of reaction heat, the reactor 1 is configured as a multi-tubular reactor including a plurality of reaction tubes 2. It is preferable that the number of the reaction tubes 2 be, for example, 1,000 to 20,000, from the viewpoint of ensuring a production volume. The material of the reaction tube is preferably SUS due to its excellent heat resistance and corrosion resistance.

The reactor 1 includes a cylindrical or rectangular cylindrical jacket 6 for cooling the reaction tubes 2 (or heating it at the start of the reaction). A heat medium introduction port 14 is provided above the lower fixing plate 13 on the side of the jacket 6, and a heat medium discharge port 15 is provided below the upper fixing plate 12 on the side of the jacket 6. A space defined by the jacket 6, the upper fixing plate 12, the lower fixing plate 13, and the outsides of the reaction tubes 2 is referred to as a shell SH. A heat medium HM for controlling the temperatures of the reaction tubes 2 is introduced from the heat medium introduction port 14, flows through the shell SH, and is discharged from the heat medium discharge port 15. The inside of the shell SH may be provided with one or more baffles for defining the flow direction of the heat medium HM to make the temperature distribution of the heat medium HM more uniform throughout the shell SH. The temperature of the heat medium HM flowing through the shell SH is measured by a shell thermometer 7. The shell thermometer 7 is preferably arranged so that a temperature measuring part thereof is located at the center of the reactor 1 (in the case of a cylindrical reactor, at the center of the cross-sectional circle and near the midpoint of the cylindrical height). The heat medium HM is preferably water (steam).

In the reaction tube 2, the raw material gas S, and a mist of an aqueous solution of an alkali metal acetate SA are supplied through the supply line 8.

The raw material gas S includes a lower olefin, such as ethylene and propylene, acetic acid, and oxygen gas. The lower olefin is preferably ethylene or propylene.

The mist of an aqueous solution of an alkali metal acetate SA can be formed by spraying the aqueous solution of an alkali metal acetate SA into the raw material gas S. The alkali metal acetate SA is preferably at least one selected from the group consisting of potassium acetate and cesium acetate. The concentration of the aqueous solution of the alkali metal acetate SA is preferably 0.1 to 20% by mass. The concentration of the aqueous solution of the alkali metal acetate SA may be increased or decreased over the course of the total reaction time. The supply rate of the alkali metal acetate SA is preferably from 2 to 200 mg/h per 1 L of the volume of the catalyst layer.

In addition to the raw material gas S and the mist of the aqueous solution of the alkali metal acetate SA, water or an inert gas or both may be supplied through the supply line 8 to the reaction tube 2. The inert gas is preferably nitrogen gas, carbon dioxide, or a mixed gas thereof.

The reaction product R, unreacted gas, etc., are extracted through the extraction line 11. The reaction product R is vinyl acetate when the raw material gas S includes ethylene, and allyl acetate when propylene.

The thermometer protection tube 3 is inserted into at least one of the reaction tubes 2 from the upper part of the reactor 1. The thermometer protection tube 3 is preferably inserted to reach the vicinity of the lower part of the reaction tube 2. The number of reaction tubes 2 into which the thermometer protection tube 3 is inserted is preferably 3 to 10. When there are a plurality of thermometer protection tubes 3, it is preferable that these thermometer protection tubes 3 be arranged uniformly or symmetrically inside the reactor 1. If there is a single thermometer protection tube 3, it is preferable that the thermometer protection tube 3 be arranged in the center of the reactor 1. In FIG. 1A, the thermometer protection tubes 3 are inserted into five reaction tubes 2 including the central reaction tube 2, and the thermometer 4 is inserted into each of the thermometer protection tubes 3.

The diameter of the thermometer protection tube 3 is preferably ⅙ to ½ of the inner diameter of the reaction tube 2, and more preferably ¼ to ½ of the inner diameter of the reaction tube 2. If the thermometer protection tube 3 is too thick, the amount of catalyst filled in the reaction tube 2 decreases, as well as the cross-sectional area through which the raw material gas S flows decreases whereby the pressure loss increases, so that the reaction amount of the reaction tube 2 into which the thermometer protection tube 3 is inserted relatively decreases, that is, the temperature rise due to the entire reaction heat of the reactor 1 and the measured value of the thermometer 4 may deviate from each other. The material of the thermometer protection tube 3 is preferably SUS due to its excellent heat resistance and corrosion resistance.

The thermometer 4 is inserted into the thermometer protection tube 3. The thermometer is preferably a thermocouple or a resistance thermometer. When a thermocouple capable of multipoint measurement is used, the catalyst layer temperature can be measured at a plurality of positions (heights) of the reaction tube 2.

The shield 5 is disposed above the reaction tube 2 into which the thermometer protection tube 3 is inserted, and is attached to the thermometer protection tube 3. The shield 5 is preferably attached to the thermometer protection tube 3 such that the thermometer protection tube 3 penetrates the shield 5. It is preferable that there be no gap between the shield 5 and the thermometer protection tube 3.

In the first embodiment, the effective projection region of the shield 5 entirely covers the inlet opening 21 of the reaction tube 2 into which the thermometer protection tube 3 is inserted. The shape and size of the shield 5 are not particularly limited as long as the effective projection region of the shield 5 entirely covers the inlet opening 21 of the reaction tube 2 into which the thermometer protection tube 3 is inserted. The shield 5 may be a disk, a rectangular plate, an elliptical plate, a cylinder, a cone, a truncated cone, or a tilted plate, or a combination thereof or a form with a part thereof missing.

The effective projection region of the shield 5 will be described with reference to FIGS. 2A to 2H showing the positional relationship between the effective projection region of the shield 5 and the reaction tube 2 into which the thermometer protection tube 3 is inserted. The effective projection region EPR of the shield 5 is an area on a reference plane RP obtained by projecting, in a perpendicular direction to the reference plane RP including the upper plane 22 of the reaction tube 2 into which the thermometer protection tube 3 is inserted and extending in parallel with the upper plane 22, an area surrounded by line segments connecting points of the shield 5 at which liquid droplets are separated from the shield 5 and drop, when the mist of the aqueous solution of the alkali metal acetate SA contacts the shield 5 and flows down as the liquid droplets.

Figure 2A:
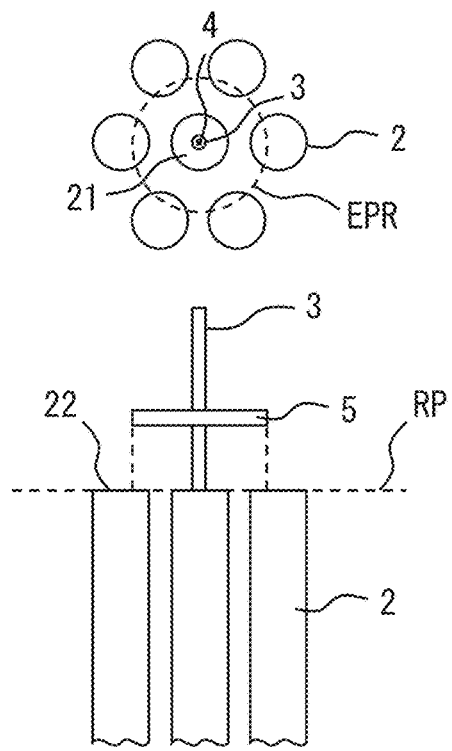
FIG. 2A It is a diagram showing the positional relationship between the effective projection region of a shield and a reaction tube into which a thermometer protection tube is inserted.

FIG. 2A shows a plurality of reaction tubes 2, a thermometer protection tube 3 inserted into the central reaction tube 2, a thermometer 4 inserted into the thermometer protection tube 3, and a disk-shaped shield 5 attached to the thermometer protection tube 3. Since the side of the shield 5 is vertical, when the mist of the aqueous solution of the alkali metal acetate SA contacts the shield 5 and flows down as a liquid droplet, the liquid droplet is separated from the lower end of the side of the shield 5 and drops along two dotted lines extending vertically in the side view on the lower side of FIG. 2A. An area on a reference plane RP obtained by projecting, in a perpendicular direction to the reference plane RP including the upper plane 22 of the reaction tube 2 into which the thermometer protection tube 3 is inserted and extending in parallel with the upper plane 22, an area surrounded by line segments connecting points of the shield 5 at which liquid droplets are separated from the shield 5 is a circular effective projection region EPR surrounded by a dotted line in the top view on the upper side of FIG. 2A. In FIG. 2A, the effective projection region EPR corresponds to the top view of the shield 5, and entirely covers the inlet opening 21 of the central reaction tube 2.

Figure 2B:
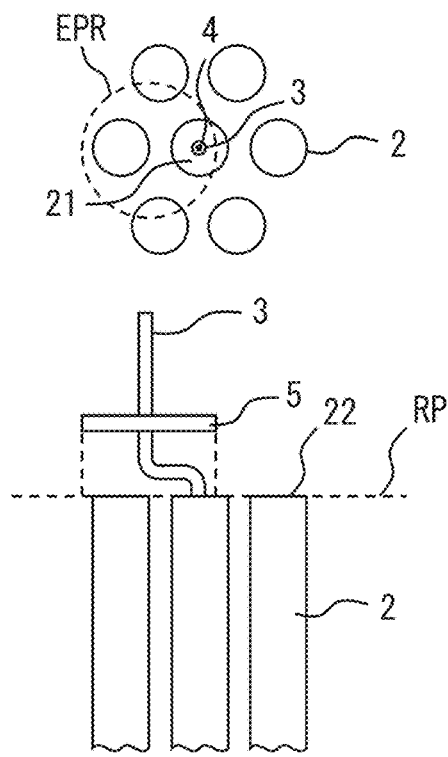
FIG. 2B It is a diagram showing the positional relationship between the effective projection region of a shield and a reaction tube into which a thermometer protection tube is inserted.

FIG. 2B shows a disk-shaped shield 5, which is the same as that of FIG. 2A, and is arranged off the center of the central reaction tube 2 and above the central reaction tube 2, since the thermometer protection tube 3 bends. Also in FIG. 2B, the effective projection region EPR corresponds to the top view of the shield 5, but does not cover all of the inlet opening 21 of the central reaction tube 2, so that a liquid droplet which drops may enter the interior of the central reaction tube 2.

Figure 2C:
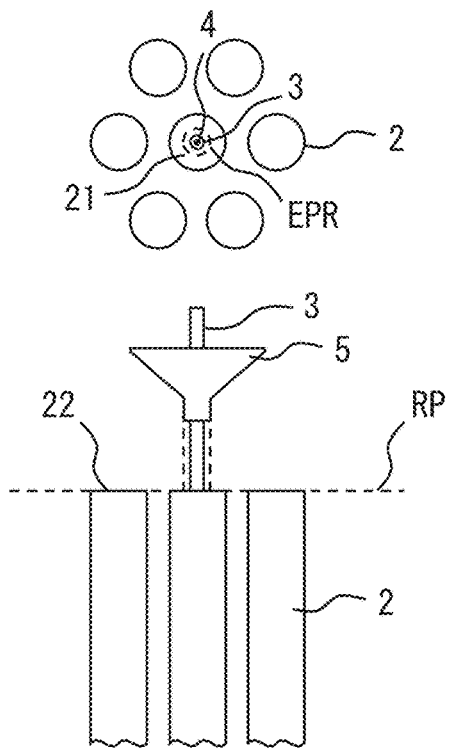
FIG. 2C It is a diagram showing the positional relationship between the effective projection region of a shield and a reaction tube into which a thermometer protection tube is inserted.

FIG. 2C shows an inverted tapered shield 5 which is a combination of a truncated cone and a cylinder. A liquid droplet flows down obliquely along the side of the shield 5 and falls off at the end of the lowermost circular area. The effective projection region EPR corresponds to the top view of the lowermost circular area of the shield 5, and covers only the vicinity of the center of the inlet opening 21 of the central reaction tube 2, so that a liquid droplet which drops may enter the interior of the central reaction tube 2.

Figure 2D:
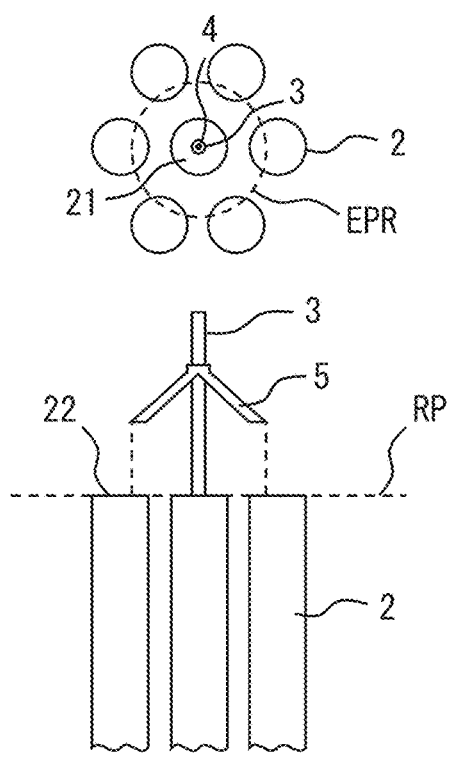
FIG. 2D It is a diagram showing the positional relationship between the effective projection region of a shield and a reaction tube into which a thermometer protection tube is inserted.

FIG. 2D shows an umbrella-shaped (the interior of a cone being hollow) shield 5. A liquid droplet flows down obliquely along the outer side of the shield 5 and falls off at the lower end of the shield 5. The effective projection region EPR corresponds to the top view of a circular area surrounded by the lower end of the shield, and entirely covers the inlet opening 21 of the central reaction tube 2.

Figure 2E:
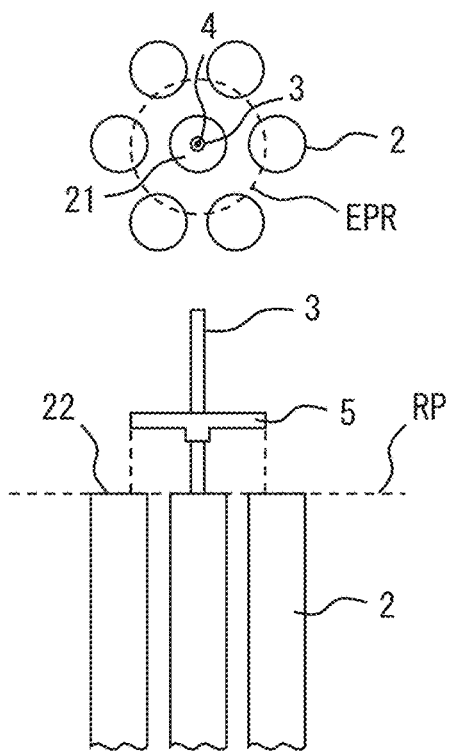
FIG. 2E It is a diagram showing the positional relationship between the effective projection region of a shield and a reaction tube into which a thermometer protection tube is inserted.

FIG. 2E shows a shield 5 in which two disks having different sizes overlap and the larger disk is located on the upper side. Since the side of the larger disk is vertical, a liquid droplet falls off at the lower end of the side of the larger disk of the shield 5, as with FIG. 2A. The effective projection region EPR corresponds to the top view of the larger disk and entirely covers the inlet opening 21 of the central reaction tube 2.

Figure 2F:
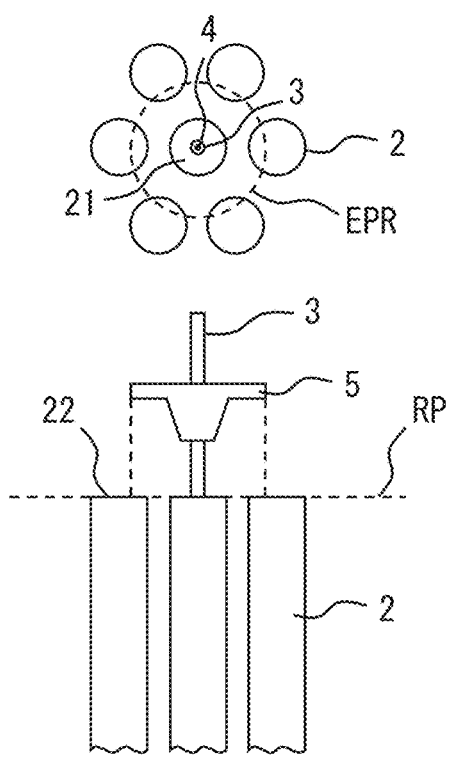
FIG. 2F It is a diagram showing the positional relationship between the effective projection region of a shield and a reaction tube into which a thermometer protection tube is inserted.

FIG. 2F shows a shield 5 in which a disk and a truncated cone are combined, the side of the disk and the conical surface of the truncated cone are discontinuous, and the disk is located on the upper side. Since the side of the disk is vertical, and the side of the disk and the conical surface of the truncated cone are discontinuous, a liquid droplet falls off at the lower end of the side of the disk of the shield 5, as with FIG. 2A. The effective projection region EPR corresponds to the top view of the disk and entirely covers the inlet opening 21 of the central reaction tube 2.

Figure 2G:
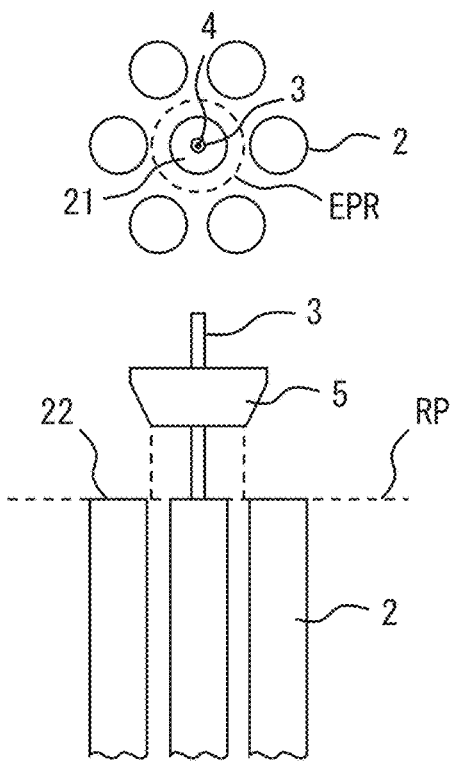
FIG. 2G It is a diagram showing the positional relationship between the effective projection region of a shield and a reaction tube into which a thermometer protection tube is inserted.

FIG. 2G shows a shield 5 in which a disk and a truncated cone are combined, the side of the disk and the conical surface of the truncated cone are continuous, and the disk is located on the upper side. Since the side of the disk and the conical surface of the truncated cone are continuous, a liquid droplet flows down obliquely along the conical surface of the truncated cone from the side of the disk and falls off at the end of the lowermost circular area. The effective projection region EPR corresponds to the top view of a circular area at the top of the truncated cone (the lowermost circular area of the shield 5), and entirely covers the inlet opening 21 of the central reaction tube 2.

Figure 2H:
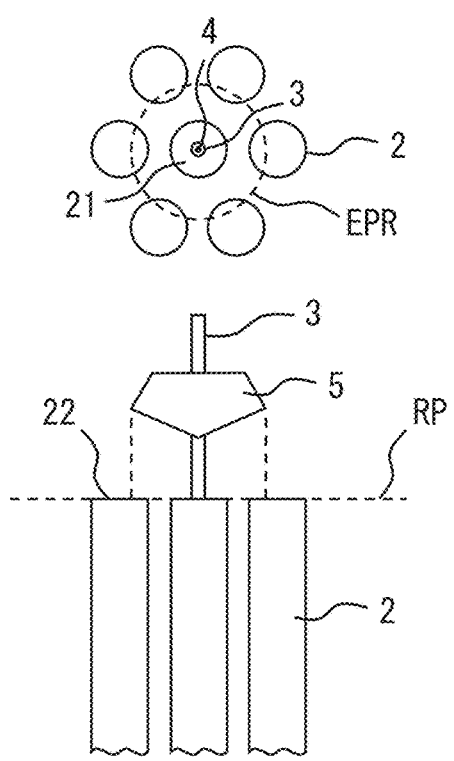
FIG. 2H It is a diagram showing the positional relationship between the effective projection region of a shield and a reaction tube into which a thermometer protection tube is inserted.

FIG. 2H shows an abacus ball-like shield in which a truncated cone and a cone are combined. A liquid droplet flows down obliquely along the conical surface of the truncated cone and falls off at the end of the circular area at the bottom of the truncated cone. The effective projection region EPR corresponds to the top view of the circular area at the bottom of the truncated cone and entirely covers the inlet opening 21 of the central reaction tube 2.

Since the size of a liquid droplet to be formed varies depending on the material, surface roughness, presence or absence of surface treatment, etc., of the shield 5, the effective projection region EPR may also vary depending on these factors. The effective projection region EPR can be determined, for example, by spraying an aqueous solution of an alkali metal acetate having a concentration to be used onto the shield 5 in an atmosphere of a reaction temperature and observing the dropping position of a liquid droplet.

The shields 5 shown in FIGS. 2A and 2D to 2H correspond to embodiments of the present invention.

Figure 3A:
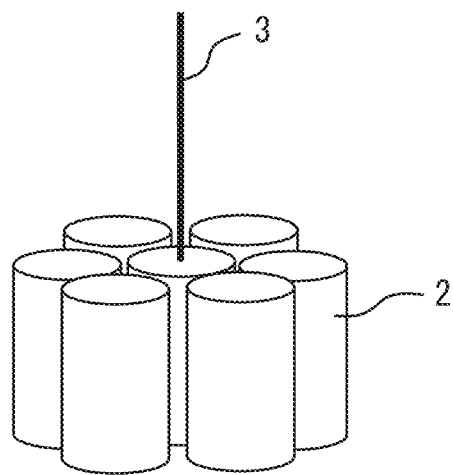
FIG. 3A It is a schematic perspective view showing an embodiment without a shield.
Figure 3B:
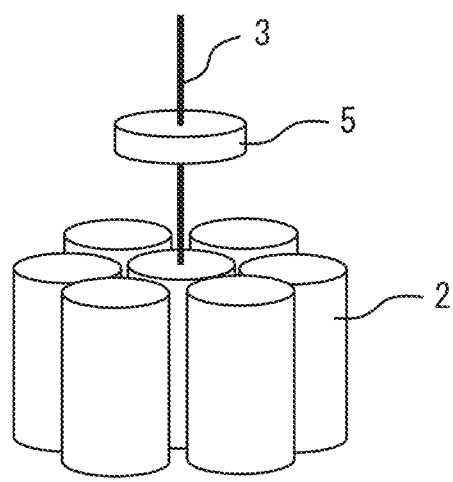
FIG. 3B It is a schematic perspective view showing the shape and size of a shield.
Figure 3C:
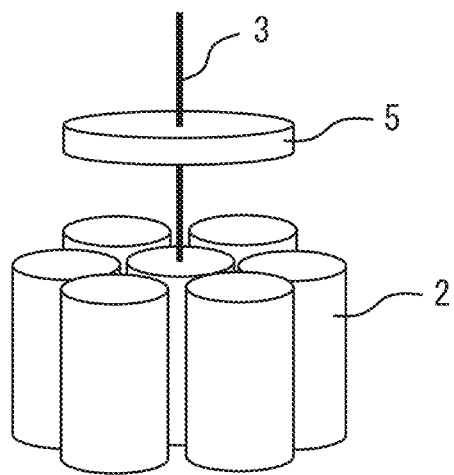
FIG. 3C It is a schematic perspective view showing the shape and size of a shield.
Figure 3D:
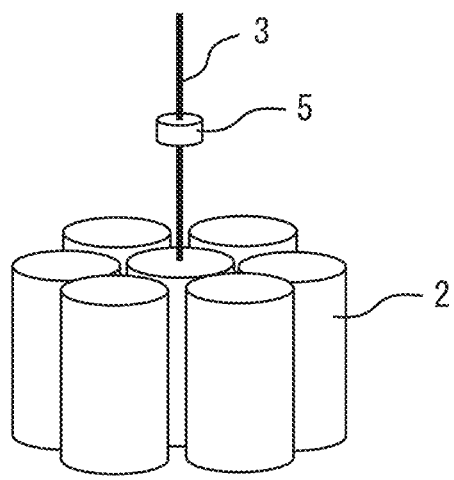
FIG. 3D It is a schematic perspective view showing the shape and size of a shield.
Figure 3E:
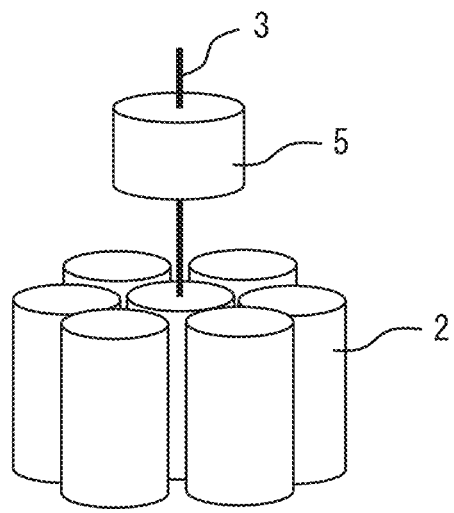
FIG. 3E It is a schematic perspective view showing the shape and size of a shield.
Figure 3F:
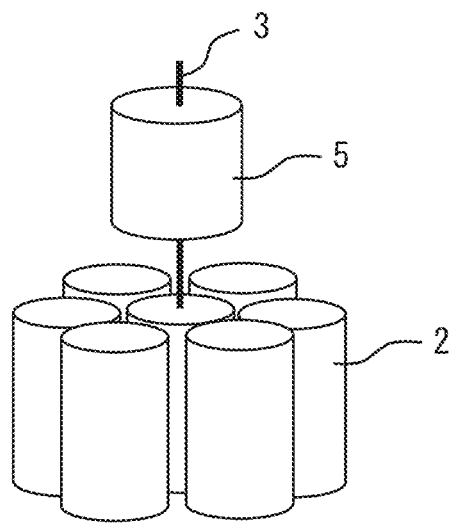
FIG. 3F It is a schematic perspective view showing the shape and size of a shield.
Figure 3G:
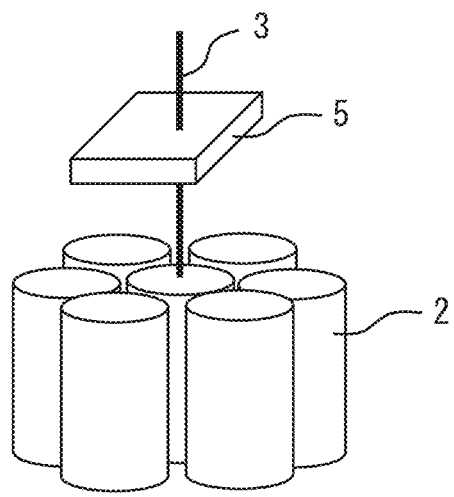
FIG. 3G It is a schematic perspective view showing the shape and size of a shield.
Figure 3H:
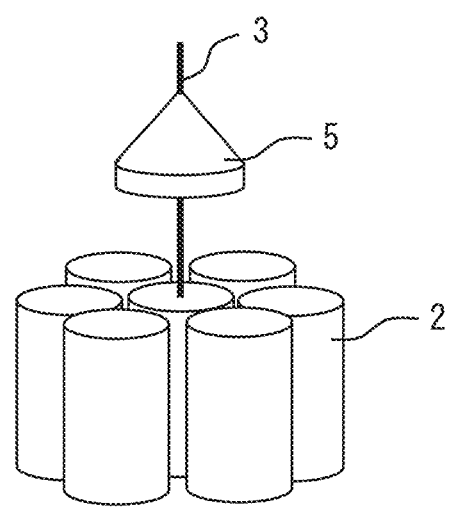
FIG. 3H It is a schematic perspective view showing the shape and size of a shield.
Figure 3I:
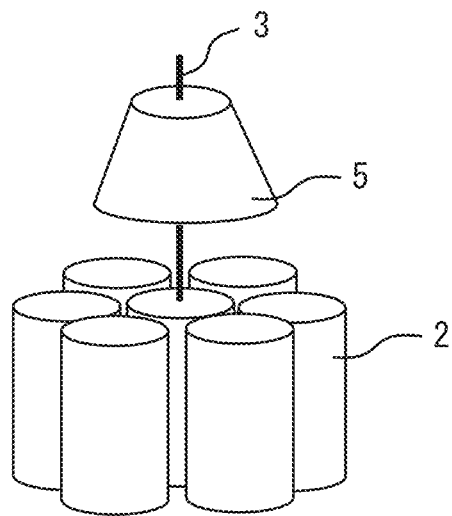
FIG. 3I It is a schematic perspective view showing the shape and size of a shield.
Figure 3J:
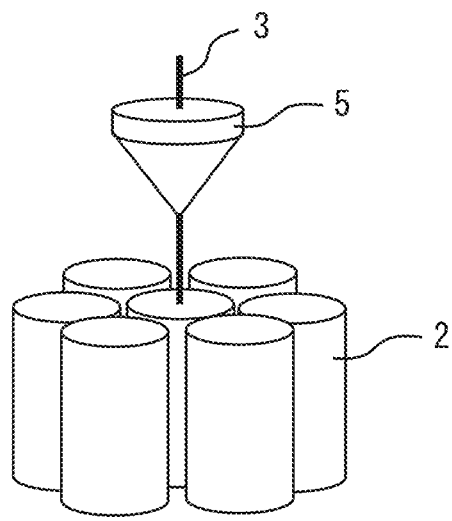
FIG. 3J It is a schematic perspective view showing the shape and size of a shield.
Figure 3K:
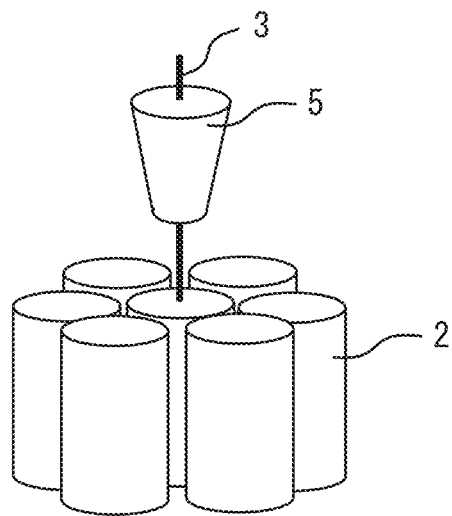
FIG. 3K It is a schematic perspective view showing the shape and size of a shield.
Figure 3L:
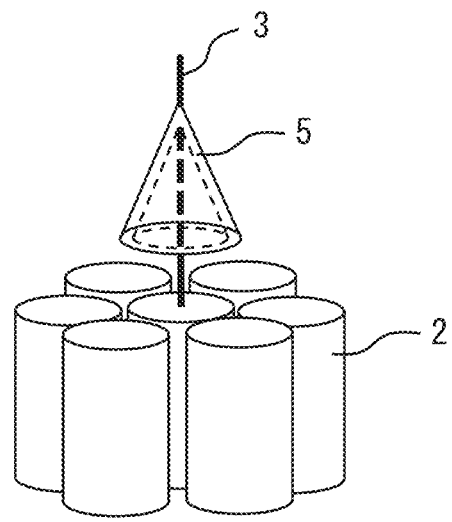
FIG. 3L It is a schematic perspective view showing the shape and size of a shield.
Figure 3M:
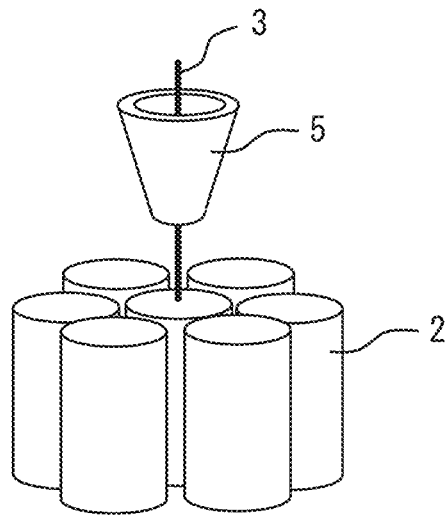
FIG. 3M It is a schematic perspective view showing the shape and size of a shield.
Figure 3N:
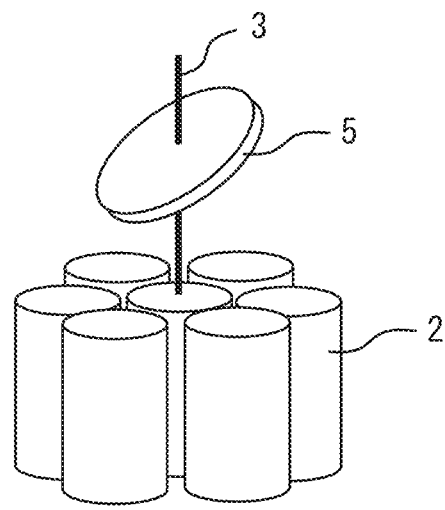
FIG. 3N It is a schematic perspective view showing the shape and size of a shield.

FIG. 3A shows an embodiment without the shield 5. FIGS. 3B to 3N show various embodiments of shapes and sizes of the shield 5. Table 1 shows the applicability of the embodiments of FIGS. 3A to 3N to the present invention.

TABLE 1

| FIG. number | Features of shield 5 | Applicability |
|---|---|---|
| 3A | No shield 5 | Not possible |
| 3B 3C | Disk with a diameter exceeding the inner diameter of reaction tube 2 | Available |
| 3D | Disk with a diameter less than the inner diameter of reaction tube 2 | Not possible |
| 3E 3F | Cylinder with a diameter exceeding the inner diameter of reaction tube | Available |
| 3G | Square plate with a length of shorter side exceeding the inner diameter of reaction tube 2 | Available |
| 3H | A combination of a cone and a disk with the area of the bottom surface being larger than the cross-sectional area of reaction tube 2 | Available |
| 3I | Truncated cone with the area of the bottom surface being larger than the cross-sectional area of reaction tube 2 | Available |

TABLE 1-continued

| FIG. number | Features of shield 5 | Applicability |
|---|---|---|
| 3J | A combination of an inverted cone and a disk with the top of the inverted cone being located at the lowest end | Not possible |
| 3K | Truncated inverted cone with the area of the bottom surface (truncated face) being smaller than the cross-sectional area of reaction tube 2 | Not possible |
| 3L | Hollow cone (cup) with the area of a region surrounding the outer periphery of the bottom being larger than the cross-sectional area of reaction tube 2 | Available |
| 3M | Truncated hollow inverted cone (cup) with the area of the bottom surface (truncated face) being smaller than the cross-sectional area of reaction tube 2 | Not possible |
| 3N | Inclined disk with the effective projection region being an ellipse larger than the cross-sectional area of reaction tube 2 | Available |

The shield 5 is preferably a disk. The disk-shaped shield 5 is preferably larger than the inner diameter of the reaction tube 2, more preferably has a diameter of more than 1.0 times and 5 times or less of the inner diameter of the reaction tube 2, and further preferably has a diameter of 1.5 times or more and 3.5 times or less of the reaction tube 2. By making the diameter of the disk-shaped shield 5 larger than the inner diameter of the reaction tube 2, it is possible to more reliably prevent a liquid droplet of the aqueous solution of the alkali metal acetate SA from entering the reaction tube 2 into which the thermometer protection tube 3 is inserted. In one embodiment, the diameter of the disk-shaped shield 5 may be 5 cm to 20 cm.

The material of the shield 5 is preferably SUS due to its excellent heat resistance and corrosion resistance.

The shield 5 is preferably arranged above the reaction tube 2 at a distance of 5 cm to 30 cm vertically from the inlet opening 21. By arranging the shield 5 at the aforementioned distance from the inlet opening 21 of the reaction tube 2, it is possible to supply an appropriate amount of a mist of the aqueous solution of the alkali metal acetate SA to the reaction tube 2 into which the thermometer protection tube 3 is inserted, while preventing a liquid droplet of the aqueous solution of the alkali metal acetate SA from entering that reaction tube 2. This can reduce the difference in an amount of reaction (catalytic activity) from the reaction tube 2 in which the thermometer protection tube 3 is not inserted, thereby increasing the accuracy of the measured value of the catalyst layer temperature.

In a second embodiment, the effective projection region EPR of the shield 5 does not overlap at all the inlet opening 21 of the reaction tube 2 into which the thermometer protection tube 3 is inserted. The effective projection region EPR of the shield 5 is as described in the first embodiment.

Figure 4:
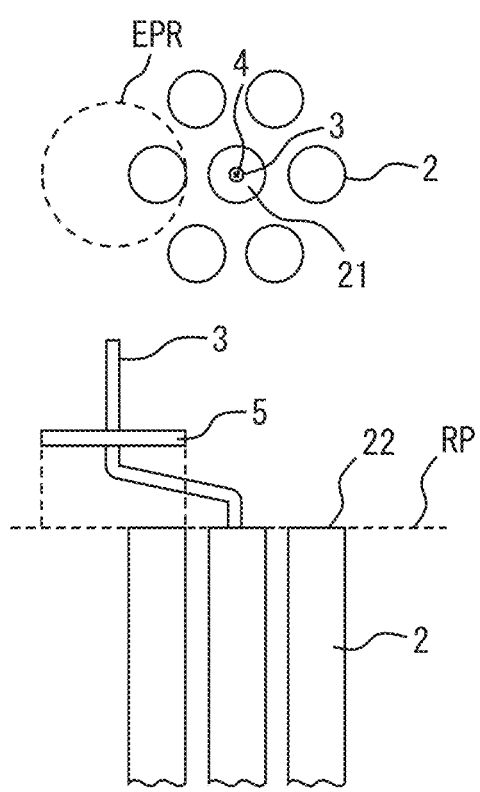
FIG. 4 It is a diagram showing the positional relationship between the effective projection region of a shield according to a second embodiment and a reaction tube into which a thermometer protection tube is inserted.

FIG. 4 shows the positional relationship between the effective projection region EPR of the shield 5 according to the second embodiment and the reaction tube 2 into which the thermometer protection tube 3 is inserted. FIG. 4 shows a disk-shaped shield 5, which is arranged off the center of the central reaction tube 2 and above this reaction tube 2, since the thermometer protection tube 3 greatly bends in the lateral direction. In FIG. 4, the effective projection region EPR corresponds to the top view of the shield 5, and does not overlap at all the inlet opening 21 of the central reaction tube 2. Therefore, a liquid droplet which drops from the shield 5 does not enter the interior of the central reaction tube 2.

In the second embodiment, the shape and size of the shield 5 are not particularly limited as long as the effective projection region EPR of the shield 5 does not overlap at all the inlet opening 21 of the reaction tube 2 into which the thermometer protection tube 3 is inserted, and can shield a liquid droplet of the aqueous solution of the alkali metal acetate SA flowing down from above the shield 5 over the thermometer protection tube 3. The shield 5 may be a disk, a rectangular plate, an elliptical plate, a cylinder, a cone, a truncated cone, or a tilted plate, or a combination thereof or a form with a part thereof missing.

In the second embodiment, the thermometer protection tube 3 may be bent to such an extent that the effective projection region EPR of the shield 5 does not overlap at all the inlet opening 21 of the reaction tube 2 into which the thermometer protection tube 3 is inserted. A combination of the shape and size of the shield 5 and the bending of the thermometer protection tube 3 may ensure that the effective projection region EPR of the shield 5 does not overlap at all the inlet opening 21 of the reaction tube 2 into which the thermometer protection tube 3 is inserted.

In the second embodiment, the shield 5 is preferably a disk. The diameter of the disk-shaped shield 5 is preferably larger than the inner diameter of the reaction tube 2, more preferably has a diameter of more than 1.0 times and 5 times or less of the inner diameter of the reaction tube 2, and further preferably has a diameter of 1.5 times or more and 3.5 times or less of the reaction tube 2. By making the diameter of the disk-shaped shield 5 larger than the inner diameter of the reaction tube 2, it is possible to prevent a liquid droplet of the aqueous solution of the alkali metal acetate SA, which is separated from the shield 5 and drops, from intensively entering one reaction tube 2. Thus, it is possible to prevent the occurrence of the reaction tube 2 in which the catalytic activity is greatly reduced as compared with the surrounding reaction tubes. In one embodiment, the diameter of the disk-shaped shield 5 may be 5 cm to 20 cm.

In the second embodiment, the material of the shield 5 is preferably SUS due to its excellent heat resistance and corrosion resistance.

In the second embodiment, the shield 5 is preferably arranged above the reaction tube 2 at a distance of 5 cm to 30 cm vertically from the inlet opening 21. By arranging the shield 5 at the aforementioned distance from the inlet opening 21 of the reaction tube 2, it is possible to supply an appropriate amount of a mist of the aqueous solution of the alkali metal acetate SA to one or more reaction tubes 2 in which the effective projection region EPR of the shield 5 overlaps the inlet opening 21. Thus, the reaction amounts (catalytic activities) of the reaction tubes 2 can be maintained more uniformly to enhance productivity.

<Catalyst for Producing Alkenyl Acetate>

A catalyst for producing an alkenyl acetate filled in the reaction tube 2 is not particularly limited as long as it is a solid catalyst, and a conventionally known catalyst can be used depending on the reaction. Examples thereof include a catalyst in which palladium is used as a main catalyst component and an alkali metal or alkaline earth metal compound is supported on a carrier as a cocatalyst, as described in the aforementioned JP H2-91045 A (Patent Literature 1).

There is no particular limitation on a method for preparing such a catalyst, and various conventionally well-known methods can be employed. A raw material used for preparing the catalyst is not particularly limited, and nitrates, carbonates, acetates, ammonium salts, oxides, halides, etc., of each element can be used in combination.

A catalyst for producing allyl acetate used in one embodiment comprises (a) palladium, (b) gold, (c) a compound containing at least one element selected from the group consisting of copper, nickel, zinc and cobalt, (d) an alkali metal acetate, and (e) a carrier.

A catalyst for producing vinyl acetate used in one embodiment comprises (a) palladium, (b) gold, (d) an alkali metal acetate, and (e) a carrier. Hereinafter, these components will be described.

(a) Palladium (a) Palladium may have any valence, and is preferably metallic palladium. The "metallic palladium" in the present disclosure is one having a valence of zero. The metallic palladium can be typically obtained by reducing a divalent or tetravalent palladium ion using a reducing agent, such as hydrazine and hydrogen. In this case, it is not necessary for all of the palladium to be in the metallic state.

There is no particular limitation on a raw material of palladium, that is, a compound containing palladium, and the metallic palladium or a palladium precursor that can be converted into the metallic palladium can be used. In the present disclosure, the metallic palladium and the palladium precursor are collectively referred to as a "palladium raw material". Examples of the palladium precursor include palladium chloride, palladium nitrate, palladium sulfate, palladium sodium chloride, palladium potassium chloride, palladium barium chloride, and palladium acetate. Palladium sodium chloride is preferably used. As the palladium precursor, a single compound may be used, or a plurality of compounds may be used in combination.

The mass ratio of (a) palladium to (e) carrier in the catalyst is preferably (a):(e)=1:10 to 1:1000, and more preferably (a):(e)=1:20 to 1:500. This ratio is defined as the ratio of the mass of the palladium element to the mass of the carrier.

(b) Gold (b) Gold is supported on the carrier in the form of a compound containing elemental gold, and it is preferable that the entirety essentially consist of metallic gold. The "metallic gold" in the present disclosure is one having a valence of zero. The metallic gold can be typically obtained by reducing a monovalent or trivalent gold ion using a reducing agent, such as hydrazine and hydrogen gas. In this case, it is not necessary for all of the gold to be in the metallic state.

There is no particular limitation on a raw material of gold, that is, a compound containing gold, and the metallic gold or a gold precursor that can be converted into the metallic gold can be used. In the present disclosure, the metallic gold and the gold precursor are collectively referred to as a "gold raw material". Examples of the gold precursor include chloroauric acid, sodium chloroaurate, and potassium chloroaurate. Chloroauric acid or sodium chloroaurate is preferably used. As the gold precursor, a single compound may be used, or a plurality of compounds may be used in combination.

The mass ratio of (b) gold to (e) carrier in the catalyst is preferably (b):(e)=1:40 to 1:65,000, more preferably (b):(e)=1:70 to 1:16,000, and further preferably (b):(e)=1:100 to 1:5,000. This ratio is defined as the ratio of the mass of the gold element to the mass of the carrier.

(c) A Compound Having at Least One Element Selected from the Group Consisting of Copper, Nickel, Zinc and Cobalt (in the Present Disclosure, Simply Referred to as a "(c) Fourth Periodic Metal Compound")

As the (c) fourth periodic metal compound, a soluble salt, such as nitrates, carbonates, sulfates, organic acid salts, halides, etc., of at least one element selected from the group consisting of copper, nickel, zinc, and cobalt, can be used. Examples of the organic acid salt include acetates. In general, compounds which are readily available and water soluble are preferable. Preferred compounds comprise copper nitrate, copper acetate, nickel nitrate, nickel acetate, zinc nitrate, zinc acetate, cobalt nitrate and cobalt acetate. Among these, copper acetate is most preferable from the viewpoint of stability of a raw material and availability. As the (c) fourth periodic metal compound, a single compound may be used, or a plurality of compounds may be used in combination.

The mass ratio of (c) fourth periodic metal compound to (e) carrier in the catalyst for producing allyl acetate is preferably (c):(e)=1:10 to 1:500, and more preferably (c):(e)=1:20 to 1:400. This ratio is defined as the ratio of the total mass of the copper, nickel, zinc and cobalt elements to the mass of the carrier.

(d) Alkali Metal Acetate

An (d) alkali metal acetate is preferably an acetate of at least one alkali metal selected from the group consisting of lithium, sodium, potassium, rubidium and cesium. Specifically, potassium acetate, sodium acetate, and cesium acetate are preferable, and potassium acetate and cesium acetate are more preferable.

The mass ratio of (d) alkali metal acetate to (e) carrier in the catalyst is preferably (d):(e)=1:2 to 1:50, and more preferably (d):(e)=1:3 to 1:40. This ratio is defined as the ratio of the mass of the alkali metal acetate used to the mass of the carrier.

(e) Carrier

There is no particular limitation on a (e) carrier, and a porous material commonly used as a carrier for a catalyst can be used. Examples of preferred carriers include silica, alumina, silica-alumina, diatomaceous earth, montmorillonite, titania and zirconia, with silica being more preferred. When a carrier containing silica as a main component is used, the silica content of the carrier is preferably at least 50% by mass, and more preferably at least 90% by weight, with respect to the mass of the carrier.

The carrier preferably has a specific surface area measured by the BET method in the range of 10 to 1000 $m^2/g$, and more preferably in the range of 100 to 500 $m^2/g$. The bulk density of the carrier is preferably in the range of 50 to 1000 g/L, and more preferably in the range of 300 to 500 g/L. The water absorption rate of the carrier is preferably from 0.05 to 3 g-water/g-carrier, and more preferably from 0.1 to 2 g-water/g-carrier. With respect to the pore structure of the carrier, the average pore diameter thereof is preferably in the range of 1 to 1000 nm, and more preferably in the range of 2 to 800 nm. When the average pore diameter is 1 nm or more, gas diffusion can be facilitated. On the other hand, when the average pore diameter is 1000 nm or less, a specific surface area of the carrier which is necessary for obtaining catalytic activity can be ensured.

There is no particular limitation on the shape of the carrier. Specific examples thereof include a powder, a sphere, and a pellet, but are not limited thereto. The optimum shape can be selected depending on the reaction type and reactor to be used, etc.

There is no particular limitation on the particle size of the carrier. When the carrier is spherical, the particle diameter thereof is preferably in the range of 1 to 10 mm, and more preferably in the range of 2 to 8 mm. When the reaction is carried out by filling the reaction tube 2 with the catalyst, the particle diameter being 1 mm or more can prevent excessive increase in pressure loss when the gas flows, so that effective gas circulation is ensured. On the other hand, the particle diameter being 10 mm or less facilitates diffusion of the raw material gas into the inside of the catalyst, so that the catalytic reaction can effectively proceed.

<Filling Catalyst for Producing Alkenyl Acetate into Reaction Tube 2>

The reaction tube 2 of the reactor 1 may be uniformly filled with the catalyst for producing an alkenyl acetate, or two or more catalyst layers containing the catalyst for producing an alkenyl acetate having different alkali metal salt amounts may be arranged so that the amount of the alkali metal acetate supported on the carrier sequentially decreases from the inlet side toward the outlet side of the reactor 1 along the flow direction of the raw material gas (reaction direction).

<Alkenyl Acetate Production>

A reaction for producing an alkenyl acetate is carried out in a gas phase using a lower olefin, acetic acid and oxygen as raw materials. For example, when the lower olefin is ethylene, the reaction formula is represented by Formula (1), and when it is propylene, the reaction formula is represented by Formula (2).

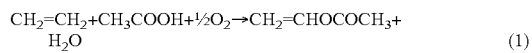

$$CH_2=CH_2+CH_3COOH+\tfrac{1}{2}O_2 \rightarrow CH_2=CHOCOCH_3+H_2O \quad (1)$$

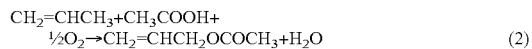

$$CH_2=CHCH_3+CH_3COOH+\tfrac{1}{2}O_2 \rightarrow CH_2=CHCH_2OCOCH_3+H_2O \quad (2)$$

The ratio of acetic acid, the lower olefin and oxygen in the raw material gas is preferably acetic acid:lower olefin:oxygen=1:0.08 to 16:0.01 to 4 in terms of a molar ratio. When the lower olefin is ethylene, it is preferable that acetic acid:ethylene:oxygen=1:0.2 to 9:0.07 to 2. When the lower olefin is propylene, it is preferable that acetic acid:propylene:oxygen=1:1 to 12:0.5 to 2.

The raw material gas comprises the lower olefin, acetic acid and oxygen gas, and may further include a diluent, such as nitrogen gas, carbon dioxide or a noble gas, if necessary. When the lower olefin, acetic acid and oxygen gas are defined as raw materials for the reaction, the ratio of the raw materials for the reaction to the diluent is preferably the raw materials for the reaction:the diluent=1:0.05 to 9, and more preferably the raw materials for the reaction:the diluent=1:0.1 to 3, in terms of a molar ratio.

The raw material gas preferably contains 0.5 to 25 mol % of water, and more preferably 1 to 20 mol % of water. Without being bound by any theory, it is believed that the presence of water in the reaction system reduces efflux of the (d) alkali metal acetate from the catalyst. Even when a large amount of water exceeding 25 mol % is present, the above effect is not improved, and hydrolysis of the generated alkenyl acetate may proceed.

The raw material gas is preferably supplied to the reactor 1 at a space velocity of 10 to 15,000 hr$^{-1}$, and more preferably 300 to 8,000 hr$^{-1}$, under standard conditions. By setting the space velocity to 10 hr$^{-1}$ or more, it is possible to appropriately remove the reaction heat. On the other hand, by setting the space velocity to less than or equal to 15,000 hr$^{-1}$, it is possible to make the facilities, such as a compressor, into a practical size.

The reaction temperature is preferably in the range of 100 to 300° C., and more preferably in the range of 120 to 250° C. The reaction temperature being 100° C. or higher can ensure the reaction rate within a practical range. The reaction temperature being 300° C. or lower enables removal of the reaction heat in a suitable manner.

The reaction pressure is preferably in the range of 0 to 3 MPaG (gauge pressure), and more preferably in the range of 0.1 to 1.5 MPaG. The reaction pressure being 0 MPaG or higher can ensure the reaction rate within a practical range. The reaction pressure being equal to or lower than 3 MPaG can suppress a cost increase in relation to the facilities, such as reaction tubes.

There is no particular limitation on the lower olefin, such as ethylene and propylene, contained in the raw material gas. In general, it is preferable to use a high purity product, but lower saturated hydrocarbons, such as methane, ethane and propane, may be mixed.

There is no particular limitation on oxygen gas. Oxygen may be supplied in a diluted form with an inert gas, such as nitrogen gas or carbon dioxide gas, for example, in the form of air, but when a gas after the reaction is circulated, it is generally advantageous to use a high concentration of oxygen, preferably oxygen having a purity of 99% by volume or more.

EXAMPLES

Hereinafter, the present invention will be further described by Examples and Comparative Examples, but the present invention is not limited by these Examples in any way.

Preparation Example 1: Preparation of Catalyst A

A spherical silica carrier (sphere diameter: 5 mm, specific surface area: 155 m$^2$/g, water absorption rate: 0.85 g-water/g-carrier, hereinafter referred to simply as a "silica carrier") was used to prepare a catalyst A by the following procedures.

Step 1

4.1 L of an aqueous solution containing 199 g of palladium sodium chloride and 4.08 g of sodium chloroaurate tetrahydrate was prepared and used as an A-1 solution. To the A-1 solution, 12 L of the silica carrier (bulk density: 473 g/L, water absorption: 402 g/L) was added, and impregnated with the A-1 solution to absorb the entire amount of the A-1 solution.

Step 2

427 g of sodium metasilicate nonahydrate was dissolved in pure water, and diluted with pure water using a graduated cylinder, so that the total amount was 8.64 L, to obtain an A-2 solution. The metal-supported carrier (A-1) obtained in Step 1 was impregnated with the A-2 solution, and allowed to stand at room temperature (23° C.) for 20 hours.

Step 3

To a slurry of the alkali-treated silica carrier (A-2) obtained in Step 2, 300 g of hydrazine monohydrate was added, gently stirred, and then allowed to stand at room temperature for 4 hours. The obtained catalyst was filtrated, and then transferred to a glass column equipped with a stopcock, and washed by flowing pure water for 40 hours. Then, drying was carried out under an air stream at 110° C. for 4 hours to obtain a metal-supported catalyst (A-3).

Step 4

624 g of potassium acetate and 90 g of copper acetate monohydrate were dissolved in pure water, and diluted with pure water using a graduated cylinder, so that the total amount was 3.89 L. To the solution, the metal-supported catalyst (A-3) obtained in Step 3 was added to absorb the entire amount of the solution. Then, drying was carried out under an air stream at 110° C. for 20 hours to obtain a catalyst A for producing allyl acetate.

The mass ratio of (a) palladium, (b) gold, (c) fourth periodic metal compound, and (d) alkali metal acetate was (a):(b):(c):(d)=1:0.024:0.39:8.5. This mass ratio is based on the mass of the component element with respect to (a), (b) and (c), and the mass of the alkali metal acetate with respect to (d). The loading amount (g) of (d) alkali metal acetate per 1 g of (e) carrier was 0.110 g/g.

The amount of alkali metal acetate in the catalyst was determined as the content of K (potassium) atoms (% by mass) using an absolute calibration curve method using X-ray fluorescence analysis (XRF) after pulverizing the catalyst to obtain a uniform powder.

Preparation Example 2: Preparation of Catalyst B

The procedures of Production Example 1 were repeated except that the amount of potassium acetate was changed from 624 g to 396 g in Step 4 to produce a catalyst B. The mass ratio of (a), (b), (c) and (d) was (a):(b):(c):(d)=1:0.024:0.39:5.4. The loading amount (g) of (d) alkali metal acetate per 1 g of (e) carrier was 0.069 g/g.

Example 1

Allyl acetate was produced using a fixed-bed multitubular reactor 1 as shown in FIG. 1. The number of reaction tubes 2 was about 5,000, and each reaction tube 2 was arranged in a hexagonal lattice. The reaction tube 2 had a length of about 6.3 m and an inner diameter of 34 mm. In the reaction tube 2, in the order from the inlet side (upper side) toward the outlet side of the raw material gas, inert balls were filled so as to have a layer length of 0.8 m at the inlet side of the raw material gas and the upstream side of the catalyst, the catalyst A having a high loading amount of potassium acetate and a higher activity was filled so as to have a layer length of 3.3 m, and the catalyst B having a low loading amount of potassium acetate and a lower activity was filled so as to have a layer length of 2.2 m.

Thermometer protection tubes 3 having an outer diameter of 8 mm and an inner diameter of 6 mm were inserted into seven of the reaction tubes 2. A disk-shaped shield 5 having a diameter of 130 mm and a thickness of 5 mm was attached to the thermometer protection tube 3 at a position 100 mm from the height of the inlet of the reactor 1. Into each thermometer protection tube 3, a multipoint thermocouple capable of measuring temperatures at different height positions (upper, middle and lower sections of the catalyst layer) was inserted as a thermometer 4, and the temperature of the catalyst layer during the reaction was monitored. The shell temperature was measured by a thermocouple arranged as a shell thermometer 7 at the center of the reactor 1.

The raw material gas having the composition shown in Table 2 was flown at a space velocity of 2000 h$^{-1}$, and the reaction was carried out at a reaction temperature of 160° C. and a reaction pressure of 0.75 MPaG (gauge pressure). An aqueous solution of potassium acetate (1.5% by mass) was sprayed into the raw material gas via a spray nozzle at a supply amount of 24 g/h.

TABLE 2

| Component | Content (% by volume) |
| --- | --- |
| Acetic acid (vaporized) | 8 |
| Propylene | 35 |
| Oxygen gas | 6 |
| Water | 18 |
| Nitrogen gas | 33 |

The reaction was continued for 7,000 hours to continuously produce allyl acetate.

Figure 5A:
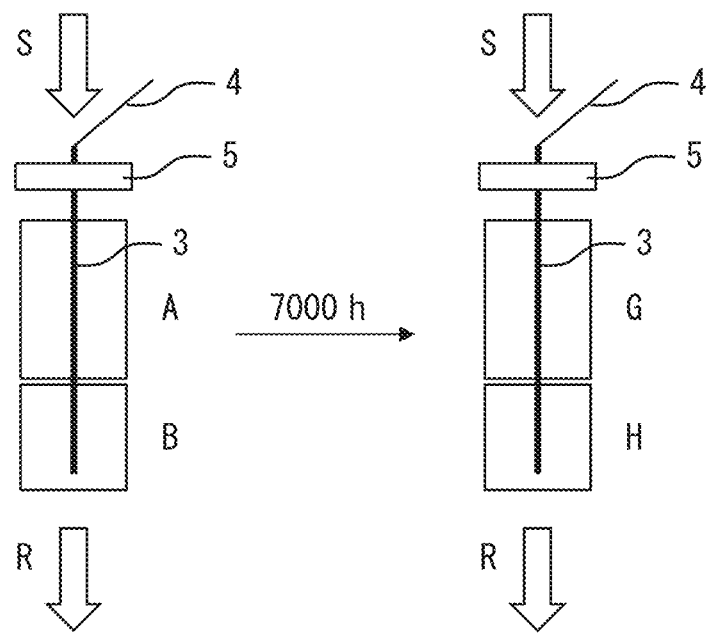
FIG. 5A It is a schematic diagram showing the state of the catalyst filled in the reaction tube of Example 1 before and after the reaction.

After completion of the reaction, the catalyst was extracted from the reaction tube 2 into which the thermometer protection tube 3 having the shield 5 attached thereto was inserted, and separated at the ratio of 3:2 from the inlet side of the raw material gas to obtain a catalyst G at the inlet side of the reaction tube 2 and a catalyst H at the outlet side of the reaction tube 2. FIG. 5A schematically shows the state of the catalyst filled in the reaction tube of Example 1 before and after the reaction.

Comparative Example 1

Allyl acetate was produced in the same manner as in Example 1, except that the thermometer protection tube 3 without the shield 5 was inserted into the reaction tube 2.

Figure 5B:
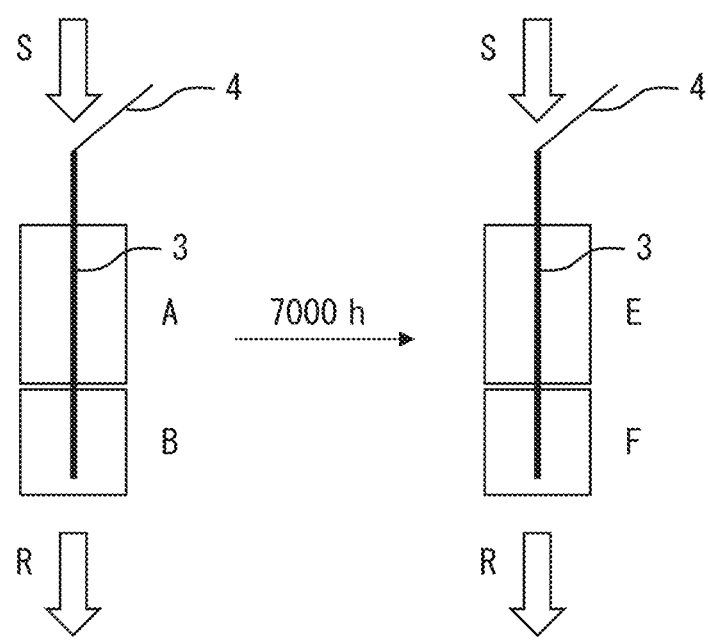
FIG. 5B It is a schematic diagram showing the state of the catalyst filled in the reaction tube of Comparative Example 1 before and after the reaction.

After the reaction, the catalyst was extracted from the reaction tube 2 into which the thermometer protection tube 3 was inserted, and separated at the ratio of 3:2 from the inlet side of the raw material gas to obtain a catalyst E at the inlet side of the reaction tube 2 and a catalyst F at the outlet side of the reaction tube 2. FIG. 5B schematically shows the state of the catalyst filled in the reaction tube of Comparative Example 1 before and after the reaction.

Reference Example 1

Figure 5C:
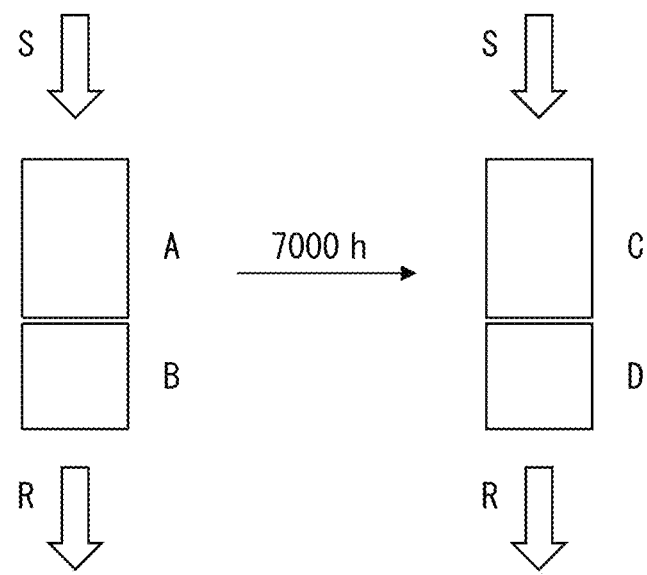
FIG. 5C It is a schematic diagram showing the state of the catalyst filled in the reaction tube of Reference Example 1 before and after the reaction.

In Example 1, the catalyst was extracted from the reaction tube 2 into which no thermometer protection tube 3 was inserted, and separated at the ratio of 3:2 from the inlet side of the raw material gas to obtain a catalyst C at the inlet side of the reaction tube 2 and a catalyst D at the outlet side of the reaction tube 2. FIG. 5C schematically shows the state of the catalyst filled in the reaction tube of Reference Example 1 before and after the reaction.

Figure 6A:
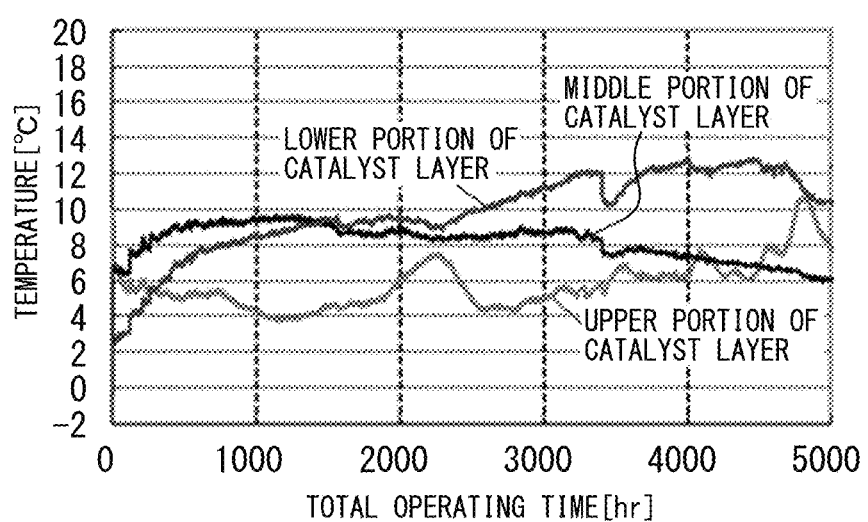
FIG. 6A It is a graph showing the relationship between the difference between the catalytic layer temperature and the shell temperature in Example 1, and the total operating time.
Figure 6B:
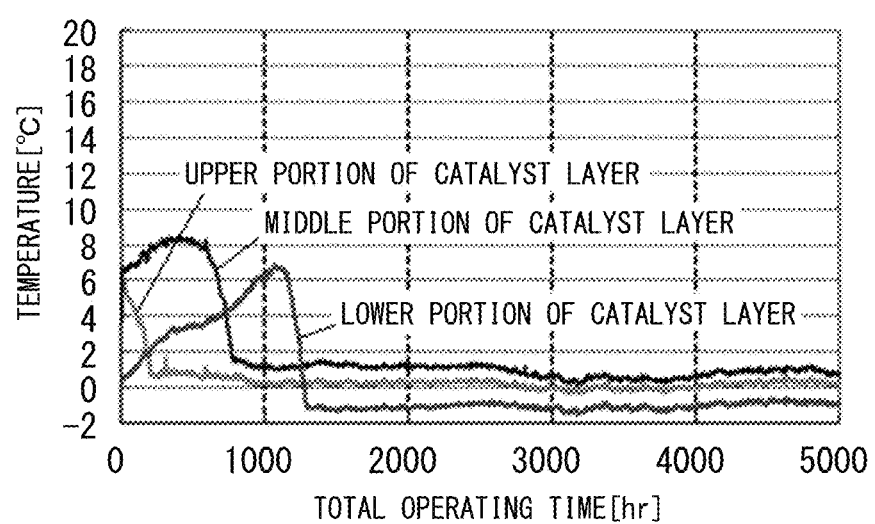
FIG. 6B It is a graph showing the relationship between the difference between the catalytic layer temperature and the shell temperature in Comparative Example 1, and the total operating time.

FIGS. 6A and 6B show the difference between the catalyst layer temperature inside the reaction tube 2 in the central part of the reactor 1 and the shell temperature during the reaction (the catalyst layer temperature—the shell temperature) in Example 1 and Comparative Example 1, respectively. Since the gas phase catalytic oxidation reaction for synthesizing allyl acetate is an exothermic reaction, when the reaction proceeds normally, the catalyst layer temperature is higher, that is, a positive temperature difference is observed.

In Comparative Example 1, although a considerable amount of allyl acetate was produced, no temperature difference was observed at 1000 hours to 1300 hours from the start of the reaction. It is presumed that this is because the catalyst of the reaction tube 2 into which the thermometer protection tube 3 was inserted was deactivated due to the presence of excessive potassium acetate, and the reaction accompanied by heat generation did not occur in this reaction tube, so that the difference from the shell temperature, which is a temperature outside the reaction tube 2, disappeared. Since the reaction proceeded normally in the reaction tube 2 into which the thermometer protection tube 3 was not inserted, allyl acetate could be produced in the reactor 1 as a whole.

On the other hand, in Example 1 in which the shield 5 was attached to the thermometer protection tube 3, the temperature difference was continuously observed even after 1000 hours from the start of the reaction. Base on this, it can be understood that, by using the shield 5, the catalyst layer temperature can be monitored correctly and continuously.

Table 3 shows the potassium (K) amounts supported on the catalysts of Example 1, Comparative Example 1, and Reference Example 1.

At the start of the reaction, the K amount supported on the catalyst A was 3.8% by mass and the K amount supported on the catalyst B was 2.5% by mass.

With regard to the catalyst after the reaction, the K amount supported on the catalyst G of Example 1, which was extracted from the reaction tube 2 into which the thermometer protection tube 3 having the shield 5 attached thereto was inserted, was 3.3% by mass, and the K amount supported on the catalyst H was 7.2% by mass. The K amount supported on the catalyst E of Comparative Example 1, which was extracted from the reaction tube 2 into which the thermometer protection tube 3 without the shield 5 was inserted, was 12.6% by mass, and the K amount supported on the catalyst F was 12.1% by mass, and excessive potassium was supported on them. The K amount supported on the catalyst C of Reference Example 1, which was extracted from the reaction tube 2 in which the thermometer protection tube 3 was not inserted, was 3.1% by mass, and the K amount supported on the catalyst D was 7.0% by mass.

Based on the above results, with respect to the K amount supported, it can be understood that the catalyst extracted from the reaction tube 2 into which the thermometer protection tube 3 not having the shield 5 attached thereto is inserted exhibits a behavior greatly different from that of most of the reaction tubes 2 into which the thermometer protection tube 3 is not inserted, and does not represent the entirety of the catalyst layers. On the other hand, it can be understood that the catalyst extracted from the reaction tube 2 into which the thermometer protection tube 3 having the shield 5 attached thereto is inserted exhibits a behavior similar to that of most of the reaction tubes 2 into which the thermometer protection tube 3 is not inserted, and represents the catalyst layers.

TABLE 3

| | Loading amount of K on catalyst (% by mass) | | | |
|---|---|---|---|---|
| | At the start of the reaction (0 hour) | | After the reaction (7000 hours) | |
| Example 1 | A | 3.8 | G | 3.3 |
| | B | 2.5 | H | 7.2 |
| Comparative Example 1 | A | 3.8 | E | 12.6 |
| | B | 2.5 | F | 12.1 |
| Reference Example 1 | A | 3.8 | C | 3.1 |
| | B | 2.5 | D | 7.0 |

INDUSTRIAL APPLICABILITY

According to the present invention, an alkenyl acetate can be produced industrially stably.

REFERENCE SIGNS LIST

1: Fixed-bed multi-tubular reactor
2: Reaction tube
3: Thermometer protection tube
4: Thermometer
5: Shield
6: Jacket
7: Shell thermometer
8: Supply line
9: Raw material gas supply
10: Reaction product discharge section
11: Extraction line
12: Upper fixing plate
13: Lower fixing plate
14: Heat medium introduction port
15: Heat medium discharge port
21: Inlet opening of reaction tube
22: Upper plane of reaction tube
S: Raw material gas
R: Reaction product
SA: Alkali metal acetate
HM: Heat medium
SH: Shell
EPR: Effective projection region
RP: Reference plane

The invention claimed is:

1. A fixed-bed multi-tubular reactor for producing an alkenyl acetate, comprising:
a plurality of reaction tubes to which a raw material gas and a mist of an aqueous solution of an alkali metal acetate are supplied from an upper part of the fixed-bed multi-tubular reactor and which each have an inlet opening and an upper plane,
a thermometer protection tube inserted into at least one of the plurality of reaction tubes from the upper part of the fixed-bed multi-tubular reactor,
a thermometer inserted into the thermometer protection tube, and
a shield disposed above the reaction tube into which the thermometer protection tube is inserted and attached to the thermometer protection tube,
wherein an effective projection region of the shield entirely covers the inlet opening of the reaction tube into which the thermometer protection tube is inserted,
wherein the effective projection region of the shield is an area on a reference plane obtained by projecting, in a perpendicular direction to the reference plane including the upper plane of the reaction tube into which the thermometer protection tube is inserted and extending in parallel with the upper plane, an area surrounded by line segments connecting points of the shield at which liquid droplets are separated from the shield and drop, when the mist of an aqueous solution of an alkali metal acetate contacts the shield and flows down as the liquid droplets.

2. The fixed-bed multi-tubular reactor according to claim 1, wherein the shield is a disk.

3. The fixed-bed multi-tubular reactor according to claim 2, wherein the diameter of the disk is larger than the inner diameter of the reaction tube.

4. The fixed-bed multi-tubular reactor according to claim 1, wherein the alkali metal acetate is at least one selected from the group consisting of potassium acetate and cesium acetate.

5. The fixed-bed multi-tubular reactor according to claim 1, wherein the number of the reaction tubes into which the thermometer protection tube is inserted is 3 to 10.

6. The fixed-bed multi-tubular reactor according to claim 1, wherein the thermometer is a thermocouple or a resistance thermometer.

7. A fixed-bed multi-tubular reactor for producing an alkenyl acetate, comprising:
a plurality of reaction tubes to which a raw material gas and a mist of an aqueous solution of an alkali metal acetate are supplied from an upper part of the fixed-bed multi-tubular reactor and which each have an inlet opening and an upper plane, a thermometer protection tube inserted into at least one of the plurality of reaction tubes from the upper part of the fixed-bed multi-tubular reactor, a thermometer inserted into the thermometer protection tube, and a shield disposed above the reaction tube into which the thermometer protection tube is inserted and attached to the thermometer protection tube, wherein an effective projection region of the shield does not overlap at all the inlet opening of the reaction tube into which the thermometer protection tube is inserted, wherein the effective projection region of the shield is an area on a reference plane obtained by projecting, in a perpendicular direction to the reference plane including the upper plane of the reaction tube into which the thermometer protection tube is inserted and extending in parallel with the upper plane, an area surrounded by line segments connecting points of the shield at which liquid droplets are separated from the shield and drop, when the mist of an aqueous solution of an alkali metal acetate contacts the shield and flows down as the liquid droplets.

\* \* \* \* \*